United States Patent [19]

Gosselink

[11] 4,394,305

[45] Jul. 19, 1983

[54] ALPHA-OXYALKYLENE AMINE OXIDE COMPOUNDS USEFUL IN DETERGENTS

[75] Inventor: Eugene P. Gosselink, Cincinnati, Ohio

[73] Assignee: The Procter & Gamble Company, Cincinnati, Ohio

[21] Appl. No.: 244,533

[22] Filed: Mar. 17, 1981

[51] Int. Cl.$^3$ .......................... C11D 3/30; C11D 3/32; C07C 103/127; C07C 69/22

[52] U.S. Cl. ..................................... 252/528; 252/546; 252/547; 260/404; 260/404.5; 560/39; 560/170; 562/434; 562/444; 562/567; 564/165; 564/194; 564/197; 564/198

[58] Field of Search ............... 564/194, 197, 198, 165; 260/404, 404.5 EO, 404.5 R; 560/39, 170; 562/434, 444, 567; 252/528, 546, 547

[56] References Cited

U.S. PATENT DOCUMENTS

| | | | |
|---|---|---|---|
| 2,159,967 | 5/1939 | Engelmann | 260/404 |
| 4,247,424 | 1/1981 | Kuzel et al. | 252/528 |
| 4,260,529 | 4/1981 | Letton | 252/547 |
| 4,301,044 | 11/1981 | Wentler et al. | 252/545 |

OTHER PUBLICATIONS

Sweeley, et al., Rearrangement and Decarboxylation Reactions of N,N-Dimethylglycine Oxide, J. Am. Chem. Soc., 79:2620–2625, (1957).
Ferris, et al., Detoxication Mechanisms, II, The Iron--Catalyzed Dealkylation of Trimethylamine Oxide, J. Am. Chem. Soc., 89:5270–5275, (1967).
Craig, et al., Tertiary Amine Oxide Rearrangements, I, Mechanism, J. Am. Chem. Soc., 83:1871–1878, (1961).

Primary Examiner—Thomas A. Waltz
Attorney, Agent, or Firm—Donald E. Hasse; Steven J. Goldstein; Jack D. Schaeffer

[57] ABSTRACT

Compounds which are carboxylic acids, or their salt, ester or amide derivatives, having an oxyalkylene amine oxide substituent at the alpha-carbon atom are disclosed. The compounds are useful as detergent surfactants which provide outstanding cleaning, particularly of oily soils, under cold water laundering conditions. Detergent compositions containing the compounds also preferably contain other surfactants, builders, and detergent adjunct materials.

35 Claims, No Drawings

ALPHA-OXYALKYLENE AMINE OXIDE COMPOUNDS USEFUL IN DETERGENTS

TECHNICAL FIELD

The present invention relates to compounds which are carboxylic acids, or their salt, ester or amide derivatives, having an oxyalkylene amine oxide substituent at the alpha-carbon atom. The compounds herein are useful as detergent surfactants which provide outstanding cleaning, particularly of oily soils, in cool or cold water (i.e., 5°–20° C.) fabric laundering operations. Detergent compositions of the present invention preferably also contain other surfactants, builders and detergent adjunct materials.

There has been considerable demand for detergent compositions capable of providing improved cleaning under cold water washing conditions. Besides the obvious economical benefits, there are many convenience and fabric care benefits to be obtained from cold water laundering. For example, dye transfer between fabrics is diminished thereby making it possible to launder mixed colored fabrics without sorting them. Laundering in cold water also results in less wrinkling of fabrics and avoids damage (e.g., shrinkage) to delicate fabrics which should not be washed in hot water.

BACKGROUND ART

U.S. Pat. No. 2,159,967, Engelmann, issued May 30, 1939, discloses carboxylic acids and their salts having an amine oxide substituent at the alpha-carbon atoms. The compounds are generally described as being surfactants which can be used for or in admixture with soaps and soap substitutes.

However, it has been found that the alpha-amine oxides have stability problems which can seriously affect their usefulness as detergent surfactants. It is believed that heavy-metal ions, such as copper, cobalt and particularly iron ions, form chelates with the alpha-amine oxides and catalyze their decomposition to relatively insoluble, non-surface active alpha-amino compounds. Trace amounts of such heavy-metal ions (e.g., on the order of parts per million or less) normally present in detergent compositions can cause substantial decomposition of the alpha-amine oxides over a period of time.

The instability of the alpha-amine oxides is also partly due to the fact that structurally they are secondary amine oxides (i.e., the carbon atom next to the amine oxide substituent is attached to 2 other carbon atoms, instead of just one carbon atom as with primary amine oxides). As such, they decompose according to the Cope elimination reaction more readily than the primary amine oxides commonly used in the detergent industry (e.g., the alkyl dimethylamine oxides). However, since the alpha-beta unsaturated acids or salts formed by Cope elimination provide some detergency, the aforementioned metal-catalyzed decomposition represents the more serious stability problem.

SUMMARY OF THE INVENTION

The present invention encompasses compounds of the formula

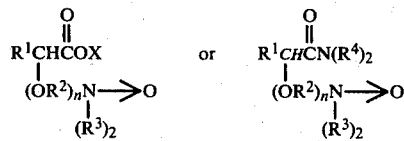

wherein $R^1$ is hydrogen or $C_1$–$C_{20}$ hydrocarbyl group; $R^2$ is a $C_2$–$C_6$ alkylene group; n is from 1 to about 20; each $R^3$ is a $C_1$–$C_{20}$ hydrocarbyl group or a $C_2$–$C_3$ alkylene oxide group containing from 1 to about 10 alkylene oxide units; each $R^4$ is hydrogen, a $C_1$–$C_{20}$ hydrocarbyl group or a $C_2$–$C_3$ alkylene oxide group containing from 1 to about 10 alkylene oxide units; and X is hydrogen, a water-soluble metal, ammonium or substituted ammonium cation, a $C_1$–$C_8$ hydrocarbyl group or a $C_2$–$C_3$ alkylene oxide group containing from 1 to about 10 alkylene oxide units; provided that the total number of carbon atoms in hydrocarbyl groups at the $R^1$, $R^3$, and X or $R^4$ substituents is from about 8 to about 40.

The invention also encompasses detergent compositions containing the above compounds.

DETAILED DESCRIPTION OF THE INVENTION

The alpha-oxyalkylene amine oxide compounds of the present invention are useful as detergent surfactants which provide outstanding cleaning, particularly of oily soils, in cool or cold water fabric laundering operations. They can, of course, also be effectively used in warm or hot water according to the desires of the user. Importantly, the alpha-oxyalkylene amine oxides herein are much more stable than the alpha-amine oxides disclosed in the art. While not intending to be limited by theory, it is believed that the incorporation of the oxyalkylene group ($OR^2$) between the alpha-carbon atom and the amine oxide group structurally prevents the present compounds from chelating with the heavy-metal ions and undergoing the metal-catalyzed decomposition. The present compounds are also primary amine oxides and thus have greater stability against Cope decomposition.

ALPHA-OXYALKYLENE AMINE OXIDE COMPOUNDS

In the general formula for the compounds herein, $R^1$ can be hydrogen or any $C_1$–$C_{20}$ hydrocarbyl group, such as a straight or branched chain alkyl, alkenyl, alkynyl, alkaryl (e.g., alkylphenyl or alkylbenzyl), or substituted hydrocarbyl (e.g., hydroxyalkyl) group. The nature of substituent $R^1$ can be varied by the selection of the parent carboxylic acid used in the reaction scheme for making the present compounds, as disclosed hereinafter. (Although the alpha-substituted alkyaryl and unsaturated carboxylic acids are not readily available by the process disclosed in U.S. Pat. No. 4,148,811, Crawford, issued Apr. 10, 1979, they can be prepared using other known reactions.) Typical carboxylic acid starting materials include acetic acid, propionic acid, butyric acid, valeric acid, caproic acid, caprylic acid, capric acid, lauric acid, myristic acid, palmitic acid, stearic acid, oleic acid, linoleic acid, linolenic acid, eicosanoic acid, mixed coconut oil fatty acids, mixed palm oil fatty acids, mixed lard fatty acids, mixed soybean oil fatty acids, and mixed tallow fatty acids, which are preferred for cost considerations. $R^1$ is preferably a $C_8$–$C_{20}$ hydrocarbyl group, and most preferably a $C_{10}$–$C_{16}$ alkyl group.

Substituent $R^2$ can be any $C_2$–$C_6$ alkylene group. For ease of synthesis of the compounds herein, it is preferred that $R^2$ be a $C_2$–$C_3$ alkylene group, and even more preferably an ethylene group.

The number of $C_2$–$C_6$ alkylene oxide units, n, is from 1 to about 20, preferably from 1 to about 10, and more preferably from 1 to about 3. The most preferred compounds herein are those in which n equals 1, since no additional stability is obtained when n is greater than 1.

Each $R^3$ substituent can be any $C_1$–$C_{20}$ hydrocarbyl group, or a $C_2$–$C_3$ alkylene, preferably ethylene, oxide group containing from 1 to about 10, preferably 1 to about 5, alkylene oxide units. Such a $C_2$–$C_3$ alkylene oxide group would commonly, and preferably, be terminated with a hydrogen atom, but also can be terminated with a methyl, ethyl or propyl group. Each $R^3$ is preferably a $C_1$–$C_4$ hydrocarbyl group, and more preferably a methyl, ethyl, 2-hydroxyethyl or 2-hydroxypropyl group.

Each $R^4$ substituent can be hydrogen, a $C_1$–$C_{20}$ hydrocarbyl group or a $C_2$–$C_3$ alkylene, preferably ethylene, oxide group containing from 1 to about 10, preferably 1 to about 5, alkylene oxide units. As before, the $C_2$–$C_3$ alkylene oxide group can be terminated with a hydrogen atom or a methyl, ethyl or propyl group. Preferably each $R^4$ is hydrogen, a $C_1$–$C_4$ hydrocarbyl group or an ethylene oxide group containing from 1 to about 5 ethylene oxide units. Most preferably, each $R^4$ is a methyl, ethyl, 2-hydroxyethyl or 2-hydroxypropyl group.

Substituent X can be hydrogen, a water-soluble metal, ammonium or substituted ammonium cation, a $C_1$–$C_8$ hydrocarbyl (e.g., alkyl, alkenyl, hydroxyalkyl) group or a $C_2$–$C_3$ alkylene oxide group containing from 1 to about 10 alkylene oxide units. The $C_1$–$C_8$ hydrocarbyl group is preferably a $C_1$–$C_4$ hydrocarbyl group, and more preferably a methyl, ethyl, 2-hydroxyethyl or 2-hydroxypropyl group. Suitable water-soluble metal cations above include any of the alkali metal and alkaline earth metal cations. Useful substituted ammonium cations include, for example, the methyl-, dimethyl-, trimethyl-, diethanol- and triethanolammonium cations and quaternary ammonium cations such as tetramethylammonium and dimethyl piperidinium cations. Preferably, X is a water-soluble alkali metal cation. Most preferably, X is sodium.

It will be appreciated that the above substituents should be selected such that the compounds herein exhibit sufficient surface activity and solubility for their intended use. Thus, the total number of carbon atoms in hydrocarbyl groups at the $R^1$, $R^3$, and X or $R^4$ substituents should be from about 8 to about 40, preferably from about 12 to about 30. Additionally, when the compounds herein, particularly the amide derivatives, have relatively long hydrocarbyl chains at the various substituents, it is preferred that they also contain more than one $C_2$–$C_3$ alkylene (preferably ethylene) oxide unit for optimum solubility, especially in cold water. For example, n should be greater than 1 or one or more of the $R^3$, X or $R^4$ substituents should be a $C_2$–$C_3$ alkylene oxide group in such compounds.

The economical practice of the present invention on an industrial scale ultimately depends on a ready source of alpha-halo carboxylic acids, from which the alpha-oxyalkylene amine oxide compounds herein are derived. Alpha-bromo carboxylic acids, which are available via the Hell-Volhard-Zelinsky reaction, are suitable starting materials. However, H-V-Z alpha-bromo acids are quite expensive. Fortunately, high quality, low cost alpha-chloro carboxylic acids suitable for use in preparing the compounds herein are available by the process disclosed in U.S. Pat. No. 4,148,811, Crawford, issued Apr. 10, 1979, incorporated herein by reference. Additionally, a preferred process for preparing 1,4-bis(dicyanomethylene) cyclohexane, the precursor of the tetracyanoquinodimethane (TCNQ) used in the above process, is disclosed in U.S. Pat. No. 4,229,364, Crawford, issued Oct. 21, 1980, incorporated herein by reference.

The following is a typical synthesis of the amine oxide of sodium alpha-dimethylaminoethoxystearate, using alpha-chlorostearic acid obtained by the process disclosed in U.S. Pat. No. 4,148,811, Crawford, as a representative starting material.

Step 1:

$$\underset{\underset{Cl}{|}}{C_{16}CHCOOH} + NaOCH_2CH_2N(CH_3)_2 \longrightarrow$$

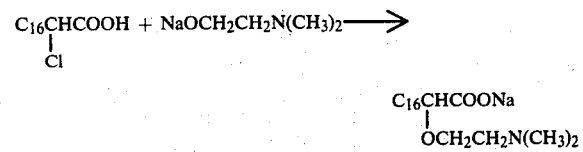

Sodium 2-dimethylaminoethoxide was preformed by mixing 5 moles of dimethylethanolamine and 2.7 moles of sodium spheres. The mixture was first cooled to control the exothermic conditions and then heated to complete the reaction of all sodium. After about 1 hour, powdered alpha-chlorostearic acid was added to the 2-dimethylaminoethoxide while maintaining the internal temperature at about 115°–125° C. for 20 minutes. Heating of the mixture was continued up to reflux and held for about 2 hours, at which point thin layer chromatography (TLC) showed the reaction to be essentially complete. The reaction mixture was cooled to 40° C. and partitioned between 1500 ml. hexane and 1300 ml. acetonitrile. The mixture was warmed to facilitate breaking of the emulsion and then was allowed to stand overnight at room temperature. The top layer was drawn off and the lower layer washed with 800 ml. hexane. The hexane layers were combined and washed with 1000 ml. acetonitrile. The hexane was stripped to a dark amber oil, which was mixed with 100 ml. hexane and 1500 ml. acetonitrile. The two phase system was treated with anhydrous hydrochloric acid until a pH of below 7 was obtained and a hot reddish solution had formed. Crystallization began and continued at room temperature. The crystals were collected on a filter and washed with 500 ml. acetonitrile. They were again crystallized from 2000 ml. acetonitrile and washed with 700 ml. acetonitrile, at which point TLC showed good purity. The undried crystals were dissolved in methanol and made basic (pH 10) with 25% sodium methoxide in methanol. The resulting slurry was cooled and filtered to remove salts. The filtrate was stripped to a very viscous oil which solidified on standing. The solid was then dissolved in 800 ml. hot tetrahydrofuran, cooled and filtered slowly to remove salts, which were washed on the filter. The total filtrate of about 1600 ml. was stirred as 600 ml. acetonitrile was added. The mixture was seeded and left stirring at room temperature overnight. The crystals were collected, washed with 400 ml. acetonitrile, and recrystallized again as above, except that the tetrahydrofuran solution was treated with dry ice to neutralize the slight excess of sodium hydroxide prior to filtering out salts. After adding acetonitrile and crystallizing, the washed crystals were oven dried to give 304 g. (66% yield) of sodium alpha-dimethylaminoethoxystearate (along with a small amount of inorganic salts).

Step 2:

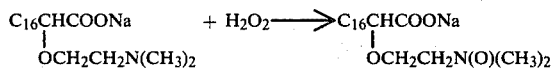

126 g. of sodium alpha-dimethylaminoethoxystearate was dissolved in 600 ml. ethanol and filtered to remove salts. The ethanol solution was treated with 60 g. of 30% hydrogen peroxide at room temperature, and then heated in a 60° C. bath for about 8 hours. TLC showed that the reaction was not quite complete so an additional 30 g. hydrogen peroxide was added and the mixture heated for 9 hours. At this point, TLC indicated only a trace of starting material left. The reaction mixture was diluted to 1 liter with methanol and the acid form was precipitated with carbon dioxide. Several precipitations were done to get as much product as possible. The acid form of the amine oxide was recrystallized from 500 ml. pyridine (heated to boiling) twice to remove what appeared to be unoxidized starting material. The crystals from the second recrystallization were washed on the filter with 100 ml. methanol (after sucking as free of pyridine as possible). The dried crystals of the acid form of the amine oxide weighed 90 g. The crystals were slurried in 300 ml. methanol and stirred as 50% sodium hydroxide was added dropwise with pH monitoring. When exactly the theoretical amount of base had been added, the pH had risen to about 8 and the solid had just dissolved. The solvent was stripped using a maximum temperature of 40° C. on a Rotovapor. The resulting thick oil was cooled to induce crystallization. The crystals were broken up and dried overnight in a vacuum oven at 45° C. After grinding to a white powder, 96 g. of the amine oxide of sodium alpha-dimethylaminoethoxystearate was obtained.

An ester of the above alpha-amine oxide carboxylate can be obtained by the following reactions. The carboxylate is dissolved in the desired alcohol and enough sulfuric acid is added to make the system acidic (approximately pH 1). The system is heated to 60°–100° C. and held there until TLC shows esterification is complete. The reaction mixture is cooled and the excess acid is carefully neutralized with cold, concentrated sodium bicarbonate solution. The excess alcohol is then stripped to give a mixture of the amine oxide carboxylic ester with salts. This mixture can be used directly or the amine oxide carboxylic ester can be separated from the bulk of the salts by extraction with an alcohol such as ethanol or isopropanol. Stripping the alcohol solvent at low temperature yields the desired ester.

The following is a typical synthesis of the amine oxide of the N,N-dimethylamide of alpha-dimethylaminoethoxystearic acid.

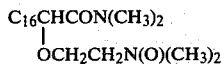

A 0.1 mole portion of sodium alpha-dimethylaminoethoxystearate is dissolved in 100 ml. toluene and treated with 0.15 mole of thionyl chloride and 5 g. of dimethylformamide. The system is gradually heated to 60° C. and held there until gas evolution ceases. The solvent is then stripped on a Rotovapor and the residue suspended in methylene chloride. The system is cooled to ice temperature and an excess of dimethylamine is added with stirring. After a few minutes, the suspension is filtered and the resulting solution stripped to give the amino amide. This is taken up in 100 ml. of methanol and treated with 2 moles of 30% hydrogen peroxide. The solution is heated to 60° C. until TLC shows the reaction is complete. Excess peroxide is destroyed by adding a little platinum oxide and then the solvent is stripped at low temperature to give the desired amide amine oxide.

As has been described above, the alpha-oxyalkylene amine oxide compounds of the present invention are particularly useful as detergent surfactants. As such, they represent from about 0.005% to about 99%, preferably from about 1% to about 40%, more preferably from about 3% to about 15%, by weight of the detergent composition. Such detergent compositions can be formulated as solids (e.g., granules, powders or laundry tablets), semi-solid pastes or gels, or liquids. They can also be impregnated in or coated on a sheet substrate, or contained in a water-soluble packet.

Detergent compositions of the present invention preferably contain one or more organic cosurfactants selected from the group consisting of anionic, cationic, nonionic, ampholytic and zwitterionic surfactants, and mixtures thereof. These surfactants are described in U.S. Pat. No. 3,929,678, Laughlin et al., issued Dec. 30, 1975, incorporated herein by reference. Useful cationic surfactants also include those described in U.S. Pat. No. 4,222,905, Cockrell, issued Sept. 16, 1980, incorporated herein by reference. The cosurfactant represents from about 0.01% to about 60%, preferably from about 1% to about 40%, more preferably from about 3% to about 20%, by weight of the detergent composition.

Preferred cosurfactants herein are the nonionic surfactants described in U.S. Pat. No. 3,929,678 from column 13, line 14 to column 16, line 6. Particularly preferred nonionic surfactants are the ethoxylated alcohols or ethoxylated alkyl phenols of the formula $R(OCH_2CH_2)_nOH$, wherein R is a $C_8$–$C_{18}$ hydrocarbyl group or a $C_8$–$C_{15}$ alkyl phenyl group and n is from about 3 to about 12. Of this group, the ethoxylated alcohols are preferred because of their superior biodegradability. Particularly preferred are ethoxylated alcohols in which R is a $C_9$–$C_{15}$ alkyl group and n is from about 4 to about 8. A preferred weight ratio of the above nonionic surfactants to the alpha-oxyalkylene amine oxide surfactants herein is from about 1:4 to about 4:1, more preferably from about 1:2 to about 2:1.

Useful anionic surfactants specifically include those described in U.S. Pat. No. 3,929,678 from column 23, line 57 to column 35, line 20, and those described in U.S. Pat. No. 4,199,483, Jones, issued Apr. 22, 1980, from column 5, line 3 to column 6, line 26, incorporated herein by reference.

Specific preferred anionics for use herein include: the linear $C_9$–$C_{15}$ alkylbenzene sulfonates (LAS); the branched $C_9$–$C_{15}$ alkylbenzene sulfonates (ABS); the tallow alkyl sulfates, the coconut alkyl glyceryl ether sulfonates; the sulfated condensation products of mixed $C_{10}$–$C_{18}$ fatty alcohols with from about 1 to about 14 moles of ethylene oxide; and the mixtures of higher fatty acid soaps containing from 10 to 18 carbon atoms.

Useful zwitterionic surfactants herein specifically include those described in U.S. Pat. No. 3,929,678 from column 19, line 36, to column 23, line 56. Preferred zwitterionic cosurfactants are the ethoxylated zwitterionic compounds described in the above patent, particularly from Column 5, line 64 to Column 12, line 53. These surfactants exhibit outstanding particulate soil removal and good oily soil removal performance. However, since they are not compatible with most anionic surfactants, they are preferably used in combination with the ester or amide derivatives of the alpha-oxyalkylene amine oxides herein, which are not anionic in character.

The detergent compositions herein optionally, but preferably, also contain from about 1% to about 95%, preferably from about 5% to about 75%, by weight of detergent builder materials. Detergency builders are generally characterized by an ability to sequester water hardness ions, particularly calcium and magnesium. They are also used to provide or assist in maintaining an alkaline pH in the washing solution.

All builders commonly taught for use in detergent compositions are suitable for use herein. Such builders include the various water-soluble alkali metal, ammonium and alkanolammonium phosphates, polyphosphates, phosphonates, polyphosphonates, carbonates, silicates, borates, polyhydroxysulfonates, polyacetates, carboxylates, and polycarboxylates. Preferred are the alkali metal, especially sodium salts of the above.

Specific examples of inorganic phosphate builders are sodium and potassium tripolyphosphate, pyrophosphate, polymeric metaphosphate having a degree of polymerization of from about 6 to 21, and orthophosphate. Examples of polyphosphonate builders are the sodium and potassium salts of ethylene diphosphonic acid, the sodium and potassium salts of ethane 1-hydroxy-1,1-diphosphonic acid and the sodium and potassium salts of ethane,1,1,2-triphosphonic acid. Other phosphorus builder compounds are disclosed in U.S. Pat. Nos. 3,159,581; 3,213,030; 3,422,021; 3,422,137; 3,400,176 and 3,400,148, incorporated herein by reference.

Examples of non-phosphorus, inorganic builders are sodium and potassium carbonate, bicarbonate, sesquicarbonate, tetraborate decahydrate, and silicate. Suitable silicate solids have a molar ratio of $SiO_2$ to alkali metal oxide in the range from about 1:2 to about 4:1, and preferably from about 1.6:1 to about 2.4:1. Useful silicates include the anhydrous silicates disclosed in U.S. Pat. No. 4,077,897, Gault, issued Mar. 7, 1978, incorporated herein by reference, which have a particle size of between about 125 and about 300 mesh, preferably from about 190 to 250 mesh. The silicates are particularly preferred in the present compositions because they provide corrosion inhibition protection to the metal parts of washing machines and also provide a certain degree of crispness and pourability to spray-dried detergent granules.

Water-soluble, non-phosphorus organic builders useful herein include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred polycarboxylate builders herein are set forth in U.S. Pat. No. 3,308,067, Diehl, issued Mar. 7, 1967 incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other useful builders herein are sodium and potassium carboxymethyloxymalonate, carboxymethyloxysuccinate, cis-cyclohexanehexacarboxylate, cis-cyclopentanetetracarboxylate phloroglucinol trisulfonate, and the copolymers of maleic anhydride with vinyl methyl ether or ethylene.

Other suitable polycarboxylates for use herein are the polyacetal carboxylates described in U.S. Pat. No. 4,144,226, issued Mar. 13, 1979 to Crutchfield, et al., and U.S. Pat. No. 4,146,495, issued Mar. 27, 1979 to Crutchfield, et al., both incorporated herein by reference. These polyacetal carboxylates can be prepared by bringing together under polymerization conditions an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Other detergency builder materials useful herein are the "seeded builder" compositions disclosed in Belgian Pat. No. 798,856, issued Oct. 29, 1973, incorporated herein by reference. Specific examples of such seeded builder mixtures are: 3:1 wt. mixtures of sodium carbonate and calcium carbonate having 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate, sodium aluminate and calcium oxide having a particle diameter of 5 microns.

Detergency builder materials useful in the present invention also include the insoluble amorphous and crystalline aluminosilicates disclosed in European Patent Application No. 80200524.9, Rodriguez, et al., filed June 9, 1980, incorporated herein by reference. Particularly useful are the aluminosilicates commonly known as Zeolites A, X, and P(B).

Particularly preferred builder systems herein comprise from about 2% to about 10% by weight of the detergent composition of sodium silicate having a molar ratio of from about 1.6:1 to about 2.4:1 and from about 10% to about 30% by weight of the detergent composition of sodium carbonate. Such builder systems posses the alkalinity and reserve alkalinity normally desired in detergent compsitions. However, the use of more than 10% by weight of the alkali metal silicates in spray-dried detergent compositions herein can present solubility problems under cold water usage conditions, especially when sodium aluminosilicate builders are also present in the composition. U.S. Pat. No. 3,985,669, Krummel, et al., issued Oct. 12, 1976, incorporated herein by reference, discloses the preferred use of low levels of silicates in detergent compositions also containing aluminosilicate builders. However, admixing powdered alkali metal silicates with spray-dried granular compositions containing the aluminosilicates reduces interactions between the silicates and aluminosilicates and thus can improve the solubility of granular detergents containing both components.

When spray-drying compositions containing the alpha-oxyalkylene amine oxides herein, it is preferred that temperatures be less than 260° C., and preferably less than 230° C., since the stability of the compounds with respect to Cope decomposition is reduced at higher temperatures. Furthermore, storage temperatures should be less than 60° C., and preferably less than 50° C., for greatest stability. Additionally, the ester derivatives of the present compounds tend to hydrolyze under aqueous basic conditions, especially when subjected to high temperatures. Thus, they preferably are not subjected to conventional alkaline crutcher-mixing and spray-drying operations. They preferably are dry mixed or agglomerated with the other detergent components, which can conveniently be spray-dried. Also, liquid compositions containing the ester derivatives preferably have a pH of close to 7 for greatest stability.

Other ingredients commonly used in detergent compositions can be included in the compositions of the present invention. These include color speckles, bleaching agents and bleach activators, suds boosters or suds suppressors, anti-tarnish and anti-corrosion agents, soil suspending agents, soil release agents, dyes, fillers, optical brighteners, germicides, pH adjusting agents, non-builder alkalinity sources, hydrotropes, enzymes, enzyme-stabilizing agents, and perfumes.

A preferred optional component in the present detergent compositions is the alkylene oxide condensation product described in U.S. Pat. No. 4,000,080, Bartolotia, et al., issued Dec. 28, 1976, particularly from column 8, line 1 through column 9, line 10, incorporated herein by reference. Such alkylene oxide condensation products, which preferably are the polyethylene glycols having a molecular weight from about 3000 to about 9000, are believed to enhance the cold water cleaning performance of the present compositions, especially on hard to remove soils such as those found on pillowcases.

The following non-limiting examples illustrate the compounds and detergent compositions of the present invention.

All percentages, parts, and ratios used herein are by weight unless otherwise specified.

EXAMPLE I

The following are granular detergent compositions according to the present invention.

| Component | A | B | C | D |
|---|---|---|---|---|
| $C_{12-13}E_5$ nonionic surfactant* | 10.0 | | | 10.0 |
| Sodium $C_{13}$ linear alkylbenzene sulfonate | | | 12.0 | |
| Amine oxide of sodium alpha-dimethylaminoethoxytallowate | 6.0 | | | |
| Amine oxide of N,N—dimethylamide of alpha-dimethylaminoethoxytallow acid | | 5.0 | | |
| Amine oxide of sodium alpha-dimethylaminoethoxycocoate | | | 6.0 | |
| Amine oxide of methyl alpha-dimethylaminoethoxycocoate | | | | 5.0 |
| Sodium tripolyphosphate | 25.0 | 25.0 | | 32.0 |
| Sodium aluminosilicate (hydrated Zeolite A, particle diameter 1-10 microns) | | 18.0 | 18.0 | |
| Sodium nitrilotriacetate | 18.0 | | 18.0 | |
| Sodium carbonate | 10.0 | 10.0 | 12.0 | 20.0 |
| Sodium silicate (1.6r) | 6.0 | 2.0 | 3.0 | 6.0 |

-continued

| Component | A | B | C | D |
|---|---|---|---|---|
| Sodium sulfate | 10.0 | 32.0 | 24.0 | 9.3 |
| Bentolite L clay** | 3.5 | | | 3.5 |
| Polyethylene glycol 6000 | | | | 0.9 |
| Water and miscellaneous | Balance to 100 | | | |

*Condensation product of $C_{12-13}$ linear primary alcohol with 5 moles (avg.) of ethylene oxide.
**A calcium bentonite clay manufactured by Georgia Kaolin Co.

Compositions A, B and C are produced by admixing all components in a crutcher to form a homogeneous mix, and then spray-drying the mix in a conventional manner at a temperature of about 220° C. In Composition D, the amine oxide and the polyethylene glycol are dry mixed with spray-dried granules containing the remaining components to form the final detergent composition.

The above compositions, when used at a level of about 1400 parts per million (ppm), provide excellent cleaning of soiled fabrics in water having a temperature of about 15° C.

EXAMPLE II

The following are heavy-duty liquid detergent compositions according to the present invention.

| Component | A | B | C | D |
|---|---|---|---|---|
| $C_{12-13}E_{6.5}$ nonionic surfactant* | 11.0 | 13.1 | 11.0 | |
| Amine oxide of sodium alpha-dimethyl-aminoethoxycocoate | 6.6 | 8.1 | | |
| Amine oxide of sodium alpha-dimethyl-aminoethoxytallowate | | | 6.6 | 10.0 |
| Sodium citrate | 9.0 | | | |
| Sodium nitrilotriacetate | | | 12.0 | |
| Potassium pyrophosphate | | 10.0 | | |
| Potassium toluene sulfonate | 6.6 | | 9.0 | |
| Phosphate Ester (Witco PS-413) | | 12.0 | | |
| Monoethanolamine | 3.6 | 3.6 | 4.0 | 4.0 |
| Coconut fatty acid | 0.5 | | | |
| Water and miscellaneous | Balance to 100 | | | |

*Condensation product of a $C_{12-13}$ linear primary alcohol with 6.5 moles (avg.) of ethylene oxide.

The above compositions are prepared simply by mixing the components and adjusting the pH to about 11.3 with sodium hydroxide. When used at a level of about 1400 ppm, they provide outstanding cleaning of soiled fabrics under cold water usage conditions.

EXAMPLE III

The following are light-duty liquid detergent compositions according to the present invention.

| Component | A | B |
|---|---|---|
| Amine oxide of N,N—diethanolamide of alpha-dimethylaminoethoxycoconutalkyl acid | 4.0 | |
| Amine oxide of sodium alpha-dimethylamino-ethoxytallowate | | 4.0 |
| Sodium coconutalkyl polyethoxylate (3 avg.) sulfate | 22.0 | 24.0 |
| Ethanol | 9.0 | 7.0 |
| Water and miscellaneous | Balance to 100 | |

The above compositions are prepared simply by mixing the components and adjusting the pH to about 7.5 with sodium hydroxide. The compositions are especially useful for cleaning dishes and other housewares.

Other compositions within the scope of the present invention are obtained by replacing the alpha-oxyalkylene amine oxides in Examples I, II and III with the corresponding compounds derived from capric acid, lauric acid, myristic acid, palmitic acid, stearic acid, oleic acid, mixed palm oil fatty acids, mixed lard fatty acids, and mixed soybean oil fatty acids.

Other compositions are obtained by replacing the above alpha-oxyalkylene amine oxides with the amine oxide of sodium alpha-tallowalkylmethylaminoethoxyacetate, the amine oxide of sodium alpha-coconutalkylmethylaminoethoxypropionate, the amine oxide of sodium alpha-dilaurylaminotriethoxyacetate, the amine oxide of N,N-dimethylamide of alpha-dimethylaminopentaethoxytallow acid, the amine oxide of N,N-diethanolamide of alpha-coconutalkylmethylaminoethoxyacetic acid, and the amine oxide of ethyl alpha-tallow-alkylmethylaminoethoxyacetate.

What is claimed is:

1. A compound of the formula:

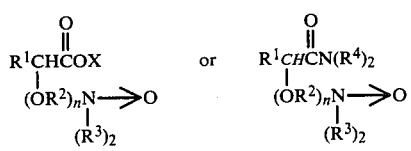

wherein $R^1$ is hydrogen or a $C_1$–$C_{20}$ hydrocarbyl group; $R^2$ is a $C_2$–$C_6$ alkylene group; n is from 1 to about 20; each $R^3$ is a $C_1$–$C_{20}$ hydrocarbyl group or a $C_2$–$C_3$ alkylene oxide group containing from 1 to about 10 alkylene oxide units; each $R^4$ is hydrogen, a $C_1$–$C_{20}$ hydrocarbyl group or a $C_2$–$C_3$ alkylene oxide group containing from 1 to about 10 alkylene oxide units; and X is hydrogen, a water-soluble metal, ammonium or substituted ammonium cation, a $C_1$–$C_8$ hydrocarbyl group or a $C_2$–$C_3$ alkylene oxide group containing from 1 to about 10 alkylene oxide units; provided that the total number of carbon atoms in hydrocarbyl groups at the $R^1$, $R^3$, and X or $R^4$ substituents is from about 8 to about 40.

2. A compound according to claim 1 wherein the total number of carbon atoms in hydrocarbyl groups at the $R^1$, $R^3$, and X or $R^4$ substituents is from about 12 to about 30.

3. A compound according to claim 1 wherein $R^1$ is a $C_{10}$–$C_{16}$ alkyl group and each $R^3$ is a $C_1$–$C_4$ hydrocarbyl group or an ethylene oxide group containing from 1 to about 5 ethylene oxide units.

4. A compound according to claim 1 wherein $R^2$ is a $C_2$–$C_3$ alkylene group.

5. A compound according to claim 4 wherein $R^2$ is an ethylene group.

6. A compound according to claim 1 wherein n is from 1 to about 10.

7. A compound according to claim 6 wherein n is from 1 to about 3.

8. A compound according to claim 7 wherein n is 1.

9. A compound according to claim 1 wherein $R^2$ is an ethylene group and n is from 1 to about 3.

10. A compound according to claim 9 wherein $R^1$ is a $C_{10}$–$C_{16}$ alkyl group and each $R^3$ is a $C_1$–$C_4$ hydrocarbyl group or an ethylene oxide group containing from 1 to about 5 ethylene oxide units.

11. A compound according to claim 10 wherein each $R^3$ is a methyl, ethyl, 2-hydroxyethyl or 2-hydroxypropyl group.

12. A compound of the formula:

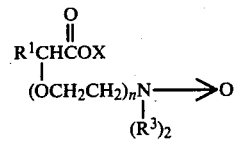

wherein $R^1$ is a $C_8$–$C_{20}$ hydrocarbyl group; n is from 1 to about 10; each $R^3$ is a $C_1$–$C_4$ hydrocarbyl group; and X is a water-soluble alkali-metal cation.

13. A compound according to claim 12 wherein $R^1$ is a $C_{10}$–$C_{16}$ alkyl group.

14. A compound according to claim 12 wherein n is from 1 to about 3.

15. A compound according to claim 12 wherein X is sodium.

16. A compound according to claim 15 wherein $R^1$ is a $C_{10}$–$C_{16}$ alkyl group and n is 1.

17. A compound according to claim 16 wherein each $R^3$ is a methyl, ethyl, 2-hydroxyethyl or 2-hydroxypropyl group.

18. A compound of the formula:

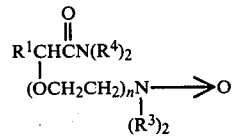

wherein R is a $C_8$–$C_{20}$ hydrocarbyl group; n is from 1 to about 10; each $R^3$ is a $C_1$–$C_4$ hydrocarbyl group; and each $R^4$ is hydrogen, a $C_1$–$C_4$ hydrocarbyl group or an ethylene oxide group containing from 1 to about 5 ethylene oxide units.

19. A compound according to claim 18 wherein $R^1$ is a $C_{10}$–$C_{16}$ alkyl group.

20. A compound according to claim 18 wherein n is from 1 to about 3.

21. A compound according to claim 18 wherein each $R^4$ is a methyl, ethyl, 2-hydroxyethyl or 2-hydroxypropyl group.

22. A compound according to claim 21 wherein $R^1$ is a $C_{10}$–$C_{16}$ alkyl group and n is 1.

23. A compound according to claim 22 wherein each $R^3$ is a methyl, ethyl, 2-hydroxyethyl or 2-hydroxypropyl group.

24. A detergent composition comprising from about 0.005% to about 99% by weight of an amine oxide surfactant of the formula:

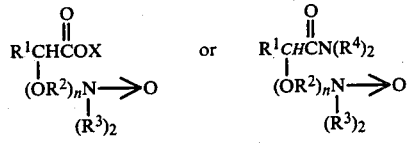

wherein $R^1$ is hydrogen or a $C_1$–$C_{20}$ hydrocarbyl group; $R^2$ is a $C_2$–$C_6$ alkylene group; n is from 1 to about 20; each $R^3$ is a $C_1$–$C_{20}$ hydrocarbyl group or a $C_2$–$C_3$ alkylene oxide group containing from 1 to about 10 alkylene oxide units; each $R^4$ is hydrogen, a $C_1$–$C_{20}$ hydrocarbyl group or a $C_2$–$C_3$ alkylene oxide group containing from 1 to about 10 alkylene oxide units; and X is hydrogen, a water-soluble metal, ammonium or substituted ammonium cation, a $C_1$–$C_8$ hydrocarbyl group or a $C_2$–$C_3$ alkylene oxide group containing from 1 to about 10 alkylene oxide units; provided that the total number of carbon atoms in hydrocarbyl groups at the $R^1$, $R^3$, and X or $R^4$ substituents is from about 8 to about 40.

25. A composition according to claim 24 comprising from about 1% to about 40% by weight of the amine oxide surfactant.

26. A composition according to claim 25 comprising from about 3% to about 15% by weight of the amine oxide surfactant.

27. A composition according to claim 24 further comprising from about 0.01% to about 60% by weight of an anionic, cationic, nonionic, ampholytic, or zwitterionic cosurfactant, or mixtures thereof.

28. A composition according to claim 27 comprising from about 3% to about 20% by weight of the cosurfactant.

29. A composition according to claim 27 wherein the cosurfactant is an ethoxylated alcohol or alkyl phenol of the formula $R(OCH_2CH_2)_nOH$, wherein R is a $C_8$–$C_{18}$ hydrocarbyl group or a $C_8$–$C_{15}$ alkyl phenyl group and n is from about 3 to about 12.

30. A composition according to claim 29 wherein R is a $C_9$–$C_{15}$ alkyl group and n is from about 4 to about 8.

31. A composition according to claim 24 further comprising from about 1% to about 95% by weight of a detergent builder material.

32. A composition according to claim 31 comprising from about 5% to about 75% by weight of the detergent builder material.

33. A composition according to claim 32 wherein the detergent builder material is selected from the group consisting of alkali metal phosphates, polyphosphates, phosphonates, polyphosphonates, carbonates, silicates, borates, polyhydroxysulfonates, polyacetates, carboxylates, polycarboxylates, and aluminosilicates, and mixtures thereof.

34. A composition according to claim 31 further comprising from about 0.01% to about 60% by weight of an anionic, cationic, nonionic, ampholytic, or zwitterionic cosurfactant, or mixtures thereof.

35. A composition according to claim 24, 27, 31 or 34 wherein, in the amine oxide surfactant, $R^1$ is a $C_{10}$–$C_{16}$ alkyl group, $R^2$ is an ethylene group, and n is from 1 to about 3, and each $R^3$ is a $C_1$–$C_4$ hydrocarbyl group.

* * * * *